US007241460B2

(12) United States Patent
Jellum et al.

(10) Patent No.: US 7,241,460 B2
(45) Date of Patent: Jul. 10, 2007

(54) STRONTIUM COMPOUND FOR TREATMENT OF SUB-DERMAL SOFT TISSUE PAIN

(75) Inventors: Egil Jellum, Olso (NO); Bjørn Jarl Fagerlund, Olso (NO); Clas Magne Kjølberg, Olso (NO); Jo Klaveness, Oslo (NO)

(73) Assignee: Santosolve AS, Oslo (NO)

(*) Notice: Subject to any disclaimer, the term of this patent is extended or adjusted under 35 U.S.C. 154(b) by 181 days.

(21) Appl. No.: 10/488,162

(22) PCT Filed: Sep. 27, 2002

(86) PCT No.: PCT/GB02/04418

§ 371 (c)(1), (2), (4) Date: Aug. 30, 2004

(87) PCT Pub. No.: WO03/028742

PCT Pub. Date: Apr. 10, 2003

(65) Prior Publication Data

US 2005/0013877 A1 Jan. 20, 2005

(30) Foreign Application Priority Data

Sep. 28, 2001 (NO) .................................. 20014746

(51) Int. Cl.

| | |
|---|---|
| ***A61K 33/00*** | (2006.01) |
| ***A61K 33/14*** | (2006.01) |
| ***A61K 33/42*** | (2006.01) |
| ***A61K 31/185*** | (2006.01) |
| ***A61K 31/19*** | (2006.01) |
| ***A61P 21/00*** | (2006.01) |
| *A61P 25/02* | (2006.01) |
| *A61P 29/00* | (2006.01) |

(52) U.S. Cl. ...................... 424/601; 424/677; 424/715; 424/718; 424/722; 514/557; 514/574; 514/936; 514/946; 514/947

(58) Field of Classification Search ................ 424/677, 424/715, 718, 722, 601; 514/557, 574, 936, 514/946, 947

See application file for complete search history.

(56) References Cited

U.S. PATENT DOCUMENTS

| | | | |
|---|---|---|---|
| 3,865,933 | A | 2/1975 | Mudge |
| 3,988,434 | A | 10/1976 | Schole et al. |
| 4,083,965 | A | 4/1978 | Bluhm |
| 4,141,359 | A | 2/1979 | Jacobsen et al. |
| 4,146,606 | A | 3/1979 | Yamaga et al. |
| 4,363,818 | A | 12/1982 | Gottlieb |
| 4,634,589 | A | 1/1987 | Scheller |
| 4,645,662 | A | 2/1987 | Nakashima et al. |
| 4,650,668 | A | 3/1987 | Barron et al. |
| 4,756,909 | A | 7/1988 | Revici |
| 4,866,046 | A | 9/1989 | Amer |
| 5,188,818 | A | 2/1993 | Merianos et al. |
| 5,234,971 | A | 8/1993 | Imai et al. |
| 5,260,289 | A | 11/1993 | Hyodo et al. |
| 5,330,746 | A | 7/1994 | Friedman et al. |
| 5,380,530 | A | 1/1995 | Hill |
| 5,716,625 | A | 2/1998 | Hahn et al. |
| 5,804,203 | A | 9/1998 | Hahn et al. |
| 5,851,512 | A | 12/1998 | Fischer |
| 5,851,556 | A | 12/1998 | Breton et al. |
| 5,855,870 | A | 1/1999 | Fischer |
| 5,856,356 | A | 1/1999 | Tsouderos et al. |
| 5,866,168 | A | 2/1999 | De Lacharriere et al. |
| 5,958,436 | A | 9/1999 | Hahn et al. |
| 5,958,462 | A | 9/1999 | McLean |
| 6,139,850 | A | 10/2000 | Hahn et al. |
| 6,168,809 | B1 | 1/2001 | De Lacharriere et al. |

FOREIGN PATENT DOCUMENTS

| | | |
|---|---|---|
| CA | 1 179 267 | 12/1984 |
| CN | 1179944 A | 4/1998 |
| EP | 0 575 841 | 6/1993 |
| EP | 0 834 319 | 4/1998 |
| WO | WO 86/03413 | 6/1986 |
| WO | WO 94/09798 | 5/1994 |
| WO | WO 96/01634 | 1/1996 |
| WO | WO 96/19184 | 6/1996 |
| WO | WO 97/48371 | 12/1997 |
| WO | WO 98/03179 | 1/1998 |
| WO | WO 98/47519 | 10/1998 |

OTHER PUBLICATIONS

The Merck Index, 12th ed., Merck & Co., Inc., Whitehouse Station, NJ, 1996, p. 551.*

Martindale The Extra Pharmacopoeia, 30th ed., The Pharmaceutical Press, London, 1993, pp. 1101-1102.*

Chemical Abstracts 110:218973 (1989).*

Chemical Abstracts 99:182515 (1983).*

Hahn et al, *American Society for Dermatologic Surgery Inc.*, 25(9):689-694 (1999).

Early et al, *Health Physics*, 69(5):677-693 (1995).

Jill Stein, "DG Dispatch—ACAAI: Strontium Supresses Itching In Allergy Skin Reactions", *Doctor's Guide* (Nov. 5, 2000).

"Cosmederm—7™", Product Information (May 25, 2002).

"Cosmederm—7™", Cosmederm Technology (May 25, 2002).

Meunier et al, "Endocrine Care", *J. of Clonical Endocrinology & Metabolism*, 87(2):2060-2066.

(Continued)

*Primary Examiner*—John Pak
(74) *Attorney, Agent, or Firm*—Sughrue, Mion, PLLC

(57) ABSTRACT

The invention provides a method of treatment of a human or non-human subject to combat sub-dermal soft tissue pain therein, said method comprising administering to a subject in need thereof an effective amount of a physiologically tolerable strontium compound.

7 Claims, No Drawings

OTHER PUBLICATIONS

Zaichik et al, No. 34810z, *Chem. Abstracts*, 70:62 (1969).
Moya-Hernandez et al, No. 131:266581g, *Chem. Abstracts, I-Pharmacology*, 131(20):26 (1999).
Ghandour et al, No. 110:142402w, *Chem. Abstracts, 68-Equilibriums, Solutions*, 110:479 (1989).
Krishnan et al, No. 90:66866b, *Chem. Abstracts*, 90:56 (1979).
Kaufmann et al, *Arch. Pharm*., 278:443-448 (1941).
Kaufmann et al, "Complex Barbituric Acid Compounds", Column 1407, *Chem. Abstracts*, vol. 32 (1937).
Perrier, "Strontium Tricitrate", Column 11860, *Chem.,Abstracts*, vol. 61 (May 1964).
Simon, *Boll. Soc. Ital. Biol. Sper*., 4:1197-1199 (1929).
Simon, *Arch. Farmacol. Sper., Chem. Abstracts*, Column 4472, vol. 28 (1934).
Yannis, No. 128:97710d, *Chem. Abstracts, 1-Pharmacology*, 128(9):68 (1998).
Neirinckx, No. 116:241750p, *Chem. Abstracts*, 116:408 (1992).
Friedman, No. 114:88683f, *Chem. Abstracts, 63-Pharmacology*, 114:445 (1991).
Surovezhin, No. 741z, *Chem. Abstracts, 5-Radiation Biochem*.., 73:63 (1970).
Gassmann, *Schweiz Med. Wochschr*., 68:291-292 (1938).
Sankaram, No. 103:105312b, *Chem. Abstracts, 34-Amino Acids, Peptides, Proteins*, 103:659 (1985).
Peppas et al, *Biomaterials*, 17(16):1553-1561 (1996).
Lehr, *Eur. J. Drug Metab. Pharmacokinet*., 21(2):139-148 (1996).
Joshi, *Ocul. Pharmacol*., 10(1):29-45 (1994).
Lehr, *Crit. Rev. Ther. Drug Carrier Syst*., 11(2-3):119-160 (1994).
Bernkop-Schnurch et al, *Adv. Drug Deliv. Rev*., 52(2):127-137 (2001).
Morishita et al, *Nippon Rinsho*, 59(11):2255-2260 (2001).
Singla et al, *J. Pharm. Pharmacol*., 53(8):1047-1067 (2001).
Bures et al, *J. Control Release*, 72(1-3):25-33 (2001).
Woodley, *Clin. Pharmacokinet*, 40(2):77-84 (2001).
Takeuchi et al, *Adv. Drug Deliv. Rev*., 47(1):39-54 (2001).
Sakuma et al, *Adv. Drug Deliv. Rev*., 47(1):21-37 (2001).
Muller et al, *Adv. Drug Deliv. Rev*., 47(1):3-19 (2001).
Ugwoke et al, *J. Pharm. Pharmacol*., 53(1):3-21 (2001).
Dostalova et al, *Ceska Slov. Farm*., 49(2):55-61 (2000).
Singla et al, *Drug Deliv. Ind. Pharm*., 26(9):913-924 (2000).
Aungst, *J. Pharma Sci*., 89(4):429-442 (2000).
Huang et al, *J. Control. Rel*., 65(1-2):63-71 (2000).
Bernkop-Schnurch, *Int. J. Pharm*., 194(1):1-13 (2000).
Hwang et al, *Crit. Rev. Ther. Drug Carrier Syst*., 15(3):243-284 (1998).
Bernkop-Schnurch, *J. Control. Rel*., 52(1-2):1-16 (1998).
Vyas et al, *Pharmazie*, 52(5):339-345 (1997).
Gwak et al, *Arch Pharm. Res*., 25(3):392-396 (2002).
Karande et al, *Pharm. Res*., 19(5):655-660 (2002).
Aguilar et al, *BMC Infect. Dis*., 2(1):9 (2002).
Touitou et al, *J. Control. Rel*., 80(1-3):1-7 (2002).
Wiechers et al, *Drug. Des. Deliv*., 6(2):87-100 (1990).
Williams et al, *Crit. Rev. Ther. Drug Carrier Syst*., 9(3-4):305-353 (1992).
Hermens, *Pharm. Weekbl. Sci*., 14(14A):253-257 (1992).
Berti et al, *Mayo Clin. Proc*., 70(6):581-586 (1995).
Bach et al, *Eur. J. Pharm. Biopharm*., 46(1):1-13 (1998).
Marjukka Suhonen et al, *J. Control Rel*., 59(2):149-161 (1999).
Kanikkannan et al, *Curr. Med. Chem*., 7(6):593-608 (2000).
Mastropaolo et al, *J. Med. Chem*., 44(2):269-273 (2001).
Moraes et al, *Br. J. Clin. Pharmacol*., 32(4):441-445 (1991).
Moraes et al, *Br. J. Clin. Pharmacol*., 31(4):423-427 (1991).
Llobet et al, *Res. Commun Chem. Pathol. Pharmacol*., 72(2):243-246 (1991).
Colomina et al, *Vet. Hum. Toxicol*., 33(2):121-124 (1991).
Llobet et al, *Arch Environ Contam. Toxicol*., 21(4):612-620 (1991).
Llobet et al, *Vet. Hum. Toxicol*., 34(1):7-9 (1992).
Delannoy et al, *Metabolism*, 51(7):906-911 (2002).
Llobet et al, *Health Phys*., 65(5):541-544 (1993).
Meunier, *Joint Bone Spine*, 68(6):576-581 (2001).
Beuhler et al, *Bone*, 29(2):176-179 (2001).
Dahl et al, *Bone*, 28(4):446-453 (2001).
Henrotin et al, *J. Bone Miner Res*., 16(2):299-308 (2001).
Canalis et al, *Bone*, 18(6):517-523 (1996).
Boivin et al, *J. Bone Miner Res*., 11(9):1302-1311 (1996).
Reinster et al, *Drugs R D*, 1(3):195-201 (1999).
Zhai et al, *Contact Dermatitis*, 42(2):98-100 (2000).
Hahn et al, *Dermatol. Surg*., 25(9):689-694 (1999).
Powis et al, *Br. Med. J*., 2(6045):1166-1168 (1976).
Kishore et al, *J. Endod*., 28(1):34-35 (2002).
Guay et al, *Pharmacotherapy*, 21(9):1070-1078 (2001).
Markowitz, *Compendium*, 14(8):1032, 1034 passim, quiz 1046 (1993).
Collaert et al, *Endod, Dent. Traumatol*., 7(4):145-152 (1991).
Mazor et al, *Clin. Prev. Dent*., 13(3):21-25 (1991).
Andronikaki-Feldani et al, *Hell Stomatol Chron*., 32(2):139-147 (1988).
Minkoff et al, *J. Periodontol*, 58(7):470-474 (1987).
Krauser, *J. Prosthet. Dent*., 56(3):307-311 (1986).
Krauser, *J. Prosthet Dent*., 56(2):153-156 (1986).
Clark et al, *J. Periodontal Res*., 20(2):212-219 (1985).
Uchida et al, *J.Peridontol*, 51(10):578-581 (1980).
Gedalia et al, *J. Peridontol*, 49(5):269-272 (1978).
Uchida et al, *Nippon Shishubyo Gakkai Kaishi*, 22(3):486-191 (1980).
Marie et al, *Calcif. Tissue Int*., 69(3):121-129 (2001).
"Facts About Sensitive Teeth", *CDS Rev*., 94(1):34 (2001).
Monaenkova et al, *Zhurnal fizicheskoy khimii*, 9(LVII):2173-2176 (1983).
Lashmar et al, *J. Pharm. Pharmacol*., 41:118-121 (1989).
Hahn, "Modulation of Neurogenic Inflammation by Strontium", *CRC Press*, pp. 261-272 (2000).
Hahn, "Anti-Irritants for Sensory Irritation", *Handbook of Cosmetic Science and Technology*, pp. 285-298 (2001).

* cited by examiner

STRONTIUM COMPOUND FOR TREATMENT OF SUB-DERMAL SOFT TISSUE PAIN

CROSS-REFERENCE TO RELATED APPLICATION

This Application is a 371 of PCT/GB02/04418, filed Sep. 27, 2002; the disclosure of which is incorporated herein by reference.

This invention relates to methods of treatment of subdermal soft tissue pain, in particular chronic pain, using strontium compounds, to the use of strontium compounds for the manufacture of medicaments for use in such methods and to novel strontium-containing pharmaceutical compositions.

Pain is a subjective experience. According to the International Association for the Study of Pain (IASP), pain is an uncomfortable sensory and emotional experience which is associated with tissue damage. The body has its own inhibitory mechanisms which use enkephalins and endorphins to suppress pain impulses. Other bodily mechanisms, in certain situations, act to intensify pain. Because pain is such a complex experience, it is not surprising that it varies from person to person or that, in the same individual, it can vary with time, place and situation.

Pains can generally be categorised as belonging to one of the following types:

nociceptive pain;
neuropathic pain;
psychogenic pain; and
idiopathic pain.

Pain can also be categorised as acute or chronic. By chronic pain is meant pain that has continued or recurred for more than 6 months and which cannot be given a causal therapy. Chronic pain sufferers can be defined as individuals experiencing pain over a prolonged period as a result for example of musculoskeletal disease, accidents (e.g. sports injuries), surgical interventions, soft tissue cancer (e.g. throat cancer), symphysis pubis disfunction, scar tissue, or disease or illness, for example rheumatism.

Throughout the world, there is a rising demand for treatments to reduce or eliminate chronic or acute pain. Current pain relieving treatments often involve medication or nerve destruction. However there remains a need for methods for relief of chronic and acute pain, especially of subdermal soft tissue pains, e.g. muscular or tendon pain, pain in scar tissue or at surgical incision sites, joint pains, chest pains, back pains, bursal pains (e.g associated with bursitis), etc, and especially methods of treatment which can be carried out by the pain sufferer without medical assistance.

Strontium compounds have been known for topical use in the treatment of itch or irritation of the skin and mucous membranes and of the teeth. Radioactive strontium compounds have also been known for use in the treatment of pain associated with metastatic bone cancers (by virtue of the effects of the radiation emitted by the strontium radionuclides).

However we have now surprisingly found that strontium compounds may also be used effectively to reduce or eliminate sub-dermal soft tissue pain.

Thus viewed from one aspect the invention provides a method of treatment of a human or non-human (e.g. vertebrate, in particular mammalian) subject to combat subdermal soft tissue pain (e.g. pain in muscle, sinew, tendon or bursae, in particular muscle pain), in particular chronic or acute pain, especially chronic pain, therein, said method comprising administering to a said subject in need thereof an effective amount of a physiologically tolerable strontium compound.

Viewed from a further aspect the invention also provides the use of a physiologically tolerable strontium compound for the manufacture of a medicament for use in the treatment of sub-dermal soft tissue pain, particularly chronic pain.

The pain treated according to the invention may for example be associated with bursitis, tendonitis, rheumatism, neuropathy, surgical intervention, injury (e.g. sports injury), scar tissue, suspected cardiac infarct, back muscles, soft tissue cancer, symphysis pubis disfunction, and musculoskeletal disease. Typically however it will not be used for treatment of headaches or stomach aches, although it can if desired.

The strontium compound used according to the invention is preferably non-radioactive. By "non-radioactive" it is meant herein that the strontium compound is not so enriched in radioactive strontium isotopes as to qualify as a radioactive material for medical purposes. While a minute proportion of the strontium present in the strontium compound may of course be radioactive, the radioactive strontium isotope content of the strontium compound should generally be no more than 1000 times the natural abundance, preferably no more than 100 times, more preferably no more than 5 times. Most preferably the strontium compound contains radioactive strontium isotopes in no more than their natural abundances.

The strontium compound used according to the present invention may be any physiologically tolerable strontium compound capable on administration of acting as a source of strontium ions. Typically, the compound will be an inorganic or organic salt or a complex, e.g. with a chelating agent. Examples of preferred compounds include chloride, nitrate, sulphate, malate, citrate, lactate, oxalate, malate, fumarate, tartrate, malonate, acetate, gluconate, glutaconate, p-aminohippurate, succinate, phosphate, hydrogenphosphate, glycerophosphate, aminocaproate, mandelate, dibenzoyltartrate, stearate, ascorbate, benzoate, 3,4-dimethoxybenzoate, and methotrexate, and complexes with penicillamine, tyrosine, leucine, etc. Especially preferably the strontium compound, if in salt form, is in the form of the chloride, nitrate, acetate, citrate, lactate or hydrogenphosphate, particularly the chloride, acetate, citrate, lactate or hydrogenphosphate, more particularly the chloride. However the strontium compound may alternatively be present in the form of a chelate complex, e.g. with a polycarboxylic acid or polyphosphoric acid compound or a cyclic polyether. Examples of appropriate chelating agents are well known in the fields of nuclear medicine and magnetic resonance imaging (see for example the scientific and patent literature from Amersham, Nycomed, Schering, Salutar, Bracco, Sterling Winthrop, Mallinckrodt, etc). The use of linear or cyclic polychelants, such as EDTA, DTPA, EGTA, DTPA-BMA, DOTA, DO3A, 1,2-di(aminoethoxy)ethane-N, N,N',N'-tetraacetic acid, Kryptofix 5 and Kryptofix 222, especially EDTA, is particularly preferred.

It is especially preferred that the strontium compound be administered together with a further analgesic, e.g. aspirin, ibuprofen, or other NSAIDs or COX-2 inhibitors, or as a salt or complex of such an analgesic.

If desired the strontium compound may be administered as a salt or complex of a drug compound having an acid or amine group, preferably such a compound with a physiological effect beneficial to a complaint suffered by the patient, e.g. one effective at treating the underlying condition responsible for the pain. In the case of amino drugs, the resulting strontium compound might typically be a strontium chelate having the amino drug as a counterion. Examples of such drug compounds include nystatin, mesalazin, sulfasalazin, olsalazin, glutaminic acid, repaglinid, pantotenic acid, epoprostenol, iloprost, tirofiban, tranexamic acid, folic acid, furosemide, bumetanide, kanrenoic acid, capopril, enalapril, lisinopril, ramipril, fosinopril, trandolapril, valsartan, telmisartan, pravastatin, fluvastatin, atorvastatin, cerivastatin, sulfadiazin, tretinoin, adapalen, azelaic acid, dinoproston, levotyroxin, lityronin, doxycyclin, lymecyclin, oxytetracyclin, tetracyclin, ampicillin, amoxicillin, mecillinam, benzylpenicillin, phenoxymethylpenicillin, diclosacillin, clocsacillin, piperacillin, clavulanic acid, tazobactam, cefaleksin, cefalotin, cefoxitin, cefuroksim, ceftazidim, ceftriaxon, aztreonam, meropenem, imipenem, cilastatin, ciprafloksasin, nalidiksinic acid, fusidenic acid, phoscarnet, and zanamivir.

Various of the strontium compounds useful in the present invention are themselves novel, in particular salts or complexes of strontium with cyclooxygenase inhibitors (other than salicylates (e.g. acetyl salicyclic acid) and oxicams (e.g. piroxicam and tenoxicam)), with amino acids, and with multidentate chelating agents (other than EDTA or EGTA) having the ability to form greater than 3, preferably greater than 4 metal coordination bonds.

Examples of appropriate cyclooxygenase inhibitors (e.g. COX1 and/or COX2 inhibitors) include NSAIDs such as amfenac, bendazac, bufexamac, cinmetacin, diclofenac etodolac, felbinac, fenbufen, fenoprofen, fentiazac, flufenamic acid, flunixin, flunoxaprofen, flurbiprofen, furprofen, ibuprofen, indomethacin, ketoprofen, lonazolac, loxoprofen, mefenamic acid, mofezolac, naproxen., and niflumic acid. The strontium salts or complexes can readily be prepared by reacting strontium carbonate with the acid form of these compounds in solution.

Thus viewed from a further aspect the invention provides a salt or complex of strontium and a physiologically tolerable non-salicylate, non-oxicam cyclooxygenase inhibitor.

Viewed from a further aspect the invention also provides a pharmaceutical composition comprising a salt or complex of strontium and a physiologically tolerable non-salicylate, non-oxicam cyclooxygenase inhibitor together with a pharmaceutical carrier or excipient.

Examples of amino acids that may be used to form strontium compounds for use according to the invention include all the natural alpha amino acids, e.g. tyrosine, leucine, lysine, etc. As with the COX inhibitors, the compounds may be prepared in solution using strontium carbonate and the amino acid. However, other strontium salts can also be used, e.g. the chloride, acetate and hydroxide.

Thus viewed from a further aspect the invention provides a salt or complex of strontium and an alpha amino acid.

Viewed from a further aspect the invention also provides a pharmaceutical composition comprising a salt or complex of strontium and an alpha amino acid together with a pharmaceutical carrier or excipient.

Examples of chelating agents which can be used to produce novel strontium compounds for use in the present invention include those with a diethylenetriamine or tetraazacyclododecane backbone carrying at least one oxyacid (e.g. carboxylic or phosphoric acid) metal binding group on the backbone nitrogens, e.g. DTPA, DTPA-bismethylamide, DOTA, DO3A, hydroxypropyl-DO3A, etc. These are well known from the diagnostic imaging contrast agent field and once again the strontium compounds can readily be prepared in solution from strontium carbonate.

Thus viewed from another aspect the invention provides a salt or complex of strontium and a physiologically tolerable diethylenetriamine- or tetraazacyclododecane-backboned chelating agent.

Viewed from a further aspect the invention also provides a pharmaceutical composition comprising a salt or complex of strontium and a physiologically tolerable diethylenetriamine- or tetraazacyclododecane-backboned chelating agent together with a pharmaceutical carrier or excipient.

In general, the strontium compound will be administered in a pharmaceutical composition comprising at least one physiologically tolerable carrier or excipient. The strontium compound may constitute up to 100% wt of the composition, preferably 0.005 to 50% wt, more preferably 0.05 to 20% wt, especially 0.1 to 10% wt, in particular 0.1 to 3% wt. Conventional pharmaceutical carriers and excipients may be used, e.g. solvents (e.g. water, ethanol, etc), tableting agents, gelling agents, preservatives, emulsifiers, redox agents (e.g. antioxidants), blowing agents, thickeners, viscosity modifiers, pH modifiers, etc.

The strontium compositions for use in the method of the invention may take any convenient administration form depending on the proposed mode of administration (e.g. oral, rectal, nasal, sub-lingual, intramuscular, intravenous, vaginal, transdermal, topical or by inhalation). Thus the compositions may for example be in the form of solutions, dispersions, suspensions, gels, liquid crystalline systems and liquid crystal precursors, emulsions, syrups, tablets, coated tablets, capsules, creams, pastes, unguents, salves, suppositories, sprays, powders, etc. For intravenous and intramuscular administration, solutions are preferred. For transdermal or topical administration, solutions, creams, pastes, unguents, emulsions and gels are preferred. For oral administration, solutions, syrups, tablets, coated tablets and capsules are preferred.

For topical administration, it is especially preferred that the composition contain a skin penetration enhancer and strontium compositions containing such penetration enhancers are novel and form a further aspect of the invention.

Thus viewed from a further aspect the invention provides a pain relieving topical pharmaceutical composition comprising a physiologically tolerable strontium compound, a physiologically tolerable carrier (e.g. an aqueous solvent, gel, paste emulsion or cream) and a physiologically tolerable skin penetration enhancing agent.

Examples of suitable skin penetration enhancing agents include propylene glycol laurate, propylene glycol monolaurate, propylene glycol monocaprylate, isopropyl myristate, sodium lauryl sulphate, dodecyl pyridinium chloride, oleic acid, propylene glycol, diethylene glycol monoethyl ether, nicotinic acid esters, hydrogenated soya phospholipids, essential oils, alcohols (such as ethanol, isopropanol, n-octanol and decanol), terpenes, N-methyl-2-pyrrolidine, alpha-tocopherol, polyethylene glycol succinate. (TPGS), Tween 80 and other surfactants, dimethyl-beta-cyclodextrin and dimethylsuiphoxide, especially DMSO.

For administration into the gastrointestinal tract or vagina, it is especially preferred that the composition contain a bioadhesive to promote prolonged contact of the composition with the mucous membranes and strontium compositions containing such bioadhesives are novel and form a further aspect of the invention.

Thus viewed from a still further aspect the invention provides a pain relieving pharmaceutical composition comprising a physiologically tolerable strontium compound and a physiologically tolerable bioadhesive, optionally together with a physiologically tolerable carrier or excipient.

The bioadhesive compositions of the invention preferably contain the strontium compound in micronized form.

Bioadhesive (i.e. mucoadhesive) agents which be used in natural or synthetic, polyanionic, polycationic or neutral, water-soluble or water-insoluble form, but are prferably large (e.g. having a molecular weight of 500 to 3000 kDa. e.g. 1000 to 2000 kDa), water-insoluble cross-linked (e.g. containing 0.05 to 2%, e.g. 0.75 to 1.5% cross-linker by weight of the total polymer, prior to any hydration), water-swellable polymers capable of forming hydrogen bonds. Preferably the bioadhesives have a mucoadhesive force greater than 100, especially preferably greater than 120, particularly greater than 150, as assessed according to the method of Smart et al. J. Pharm. Pharmacol. 36: p295-299 (1984), expressed as a percent relative to a standard in vitro.

Appropriate bioadhesives include, but are not limited to poly(carboxylic acid-containing) based polymers, such as poly(acrylic, maleic, itaconic, citraconic, hydroxyethyl methacrylic or methaorylic) acid which have strong hydogen-bonding groups, or derivatives thereof such as salts and esters. Alternatively, cellulose derivatives may be used such as methyl cellulose, ethyl cellulose, methylethyl cellulose, hydroxymethyl cellulose, hydroxyethyl ethyl cellulose, carboxymethyl cellulose, hydroxypropylmethyl cellulose or cellulose esters or ethers or derivatives or salts thereof. Other naturally occurring or synthetic polymers may also be used such as gums, e.g. xanthan gum, guar gum, locust bean gum, tragacanth gum, karaya gum, ghatti gum, cholla gum, psillium seed gum and gum arabic; clays such as montmorillonite clays, e.g. Veegum, attapulgite clay; polysaccharides such as dextran, pectin, amylopectin, agar, mannan or polygalactonic acid or starches such as hydroxypropyl starch or carboxymethyl starch; lipophilic formulations containing polysaccharides, e.g. Orabase (Bristol Myers Squibb); carbohydrates, optionally polysubitituted with groups such as sulphate, phosphate, sulphonate or phosphonate, e.g. sucrose octasulphate; polypeptides such as casein, gluten, gelatin, fibrin glue; chitosan (lactate or glutamate) or carboxymethyl chitin; glycosaminoglycans such as hyaluronic acid; metal or water soluble salts of alginic acid such as sodium alginate or magnesium alginate; schleroglucan; adhesives containing bismuth oxide or aluminium oxide; atherocollagen; polyvinyl polymers such as polyvinyl alcohols, polyvinylmethyl ethers, polyvinylpyrrolidone, polycarboxylated vinyl polymers (such as polyacrylic acids as mentioned above); polysiloxanes, polyethers; polyethylene oxides and glycols; polyalkoxides and polyacrylamides and derivatives and salts thereof.

Bioadhesives may also be used which bind to the epithelial cell layer lying below the mucous layer. This allows more specific and longer lasting adhesion due to the slower relative turnover of epithelial cells compared to mucous turnover (days rather than hours). Thus for example, receptor-mediated interactions may be achieved using plant or bacterial lectins, i.e. (glyco) proteins of non-immune origin which bind to polysaccharides or glycoconjugates, which specifically bind to sugar moieties of the epithelial cell membrane. Also so-called "reverse" lectins of mammals in which receptors on the epithelial cell binds to sugars of the agent which is added, may be used. Other bioadhesives (e.g. adhesion or invasion factors (e.g. bacterial adhesins or invasins which bind to integrins) from bacteria or viruses may be used to allow selectively for particular tissues, phenotypes, disorders etc. by binding to only certain epithelial cells.

The above described polymeric bioadhesives may also be cross-linked and may be in the form of copolymers. Preferably poly(acrylic acid) polymers (or copolymers, e.g. with di- or poly-functional allyl ethers or acrylates to make the polymer insoluble), which have preferably been cross-linked, e.g. using a polyalkenyl polyether, may be employed which have a high molecular weight and are thixotropic. Appropriate bioadhesives having this form are availabe commercially (e.g. from Goodrich) as polycarbophil, e.g. Noveon AA-1, Carbomer (Carbopol), e.g. Carbopol EX165, EX214, 434, 910, 934, 934P, 940, 941, 951, 974P and 1342.

Some of the preferred bioadhesives thus include, polyacrylic hydrogels, chitosan, polyvinyl alcohol, hydroxypropyl cellulose, hydroxypropyl methyl cellulose, sodium alginate, scleroglucan, xanthan gum, pectin, Orabase and polygalactonic acid.

One particularly effective method of transdermal delivery of strontium ions is iontophoresis. Iontophoretic assemblies containing strontium are novel and form a further aspect of the invention.

Thus viewed from a still further aspect the invention provides an iontophoretic assembly comprising a cathode in electrical contact with a drug reservoir, characterized in that said drug reservoir contains a physiologically tolerable strontium compound.

In the iontophoretic assemblies of the invention, the cathode is preferably a silver electrode and the strontium compound is preferably strontium chloride as the electrode reaction in this way produces insoluble silver chloride. The drug reservoir preferably comprises an aqueous gel containing the strontium compound in dissolved form. The assembly furthermore preferably also comprises a passive skin contact electrode and an electrical power source, e.g. a battery.

The inventors have also surprisingly found that strontium compounds, e.g. of the type described herein, are effective at combatting the pain associated with herpetic infections, in particular herpes zoster (e.g. shingles) and herpes simplex. The strontium compound may be applied topically or given orally or by injection; preferably however it is applied topically. Thus viewed from a further aspect the invention provides the use of a physiologically tolerable strontium compound for the manufacture of a medicament for use in the treatment of herpetic infection. Viewed from a further aspect the invention provides a method of treatment of a human or other mammalian subject experiencing symptoms of herpetic infection, said method comprising administering to said subject an effective amount of a physiologically tolerable strontium compound.

The invention is illustrated further in the following non-limiting Examples.

EXAMPLE 1

Composition

A strontium-containing composition was prepared as a 0.1% wt solution of strontium chloride hexahydrate in water.

EXAMPLE 2

Composition

A strontium-containing composition was prepared as a solution in water of 0.1% wt strontium chloride hexahydrate, 0.1% wt of magnesium chloride hexahydrate and 0.1% wt calcium chloride dihydrate.

EXAMPLE 3

Treatment 30 patients with pain around the sternum were asked to complete a questionnaire (a VAS form) to indicate subjectively their level of pain about the sternum. Thereafter the sternum was palpated and a further VAS form was completed to indicate the objective level of pain. The patients were subjected to a spirometric test (MVV) and thermography before treatment according to the invention.

The patients were divided into three groups, one to receive the composition of Example 1, the second to receive the composition of Example 2 and the third to receive a placebo composition (water).

The compositions were applied to the chest (sternum) of the patients by the patients themselves three times per day over a period of two weeks. The liquids were allowed to dry on the skin.

The patients completed daily VAS forms at the treatment times. For a further week the patients wiped a cotton wool pad soaked in the composition evenly over their sternums. The patients were met for weekly control and objective VAS assessment. Following the treatment period, the patients were again subjected to MVV and thermography.

The result of the study was that the patients receiving the strontium compositions had reduced levels of pain. The average VAS value for pain before treatment was 7 to 8 while after strontium treatment it had dropped to 1 to 2. Placebo treatment showed no effect.

In a further case, gargling with a 0.1% wt strontium chloride solution provided significant pain relief to a patient with throat cancer.

EXAMPLE 4

Production of Strontium a (II) Complex of Ethylenediamine Tetraacetic Acid (SrEDTA)

A suspension of strontium carbonate (1.0 g, 6.77 mmol) and ethylenediamine tetraacetic acid (1.98 g, 6.77 mmol) in water (25 ml) was stirred at 70° C. for 30 minutes. The clear solution was evaporated to dryness and dried in vacuo at ambient temperature. The title compound was isolated as a white crystalline material. Yield 2.79 g (109% calculated as anhydrous product). Melting point above 250° C.

EXAMPLE 5

Production of the Strontium (II) Complex of ethylene-bis (oxyethylenenitrilo) tetraacetic acid (SrEGTA)

A suspension of strontium carbonate (1.0 g, 6.77 mmol) and ethylenebis(oxyethylenenitrilo)tetraacetic acid (2.58 g, 6.77 mmol) in water (25 ml) was stirred at 70° C. for 6.5 hours. The solution became almost clear. The solution was filtered at room temperature and the filtrate was evaporated to dryness and dried in vacuo at ambient temperature. The title compound was isolated as a white crystalline material. Yield 1.54 g (49%).

EXAMPLE 6

Production of Strontium (II) Salicylate

A suspension of strontium carbonate (1.0 g, 6.77 mmol) and salicylic acid (1.87 g, 13.5 mmol) in water (25 ml) was stirred for 4 hours. The solution became pale yellow and almost clear. The solution was filtered at room temperature and the filtrate was evaporated to dryness and dried in vacuo at ambient temperature. The title compound was isolated as a pale red powder. Yield 2.1 g (86%). Melting point above 300° C.

EXAMPLE 7

Production of the Strontium (II) Complex of Diethylenetriaminepentaacetic Acid (SrDTPA)

A suspension of strontium carbonate (1.0 g, 6.77 mmol) and diethylenetriaminepentaacetic acid (2.67 g, 6.77 mmol) in water (25 ml) was stirred at 80° C. for 19 hours. The insoluble part was filtered off at room temperature and the filtrate was evaporated to dryness and dried in vacuo at ambient temperature. The title compound was isolated as a white/pale yellow crystalline material. Yield 1.6 g (49%). Melting point approx. 250° C.

The title compound was also prepared in 51% yield using a similar procedure with strontium acetate instead of strontium carbonate.

EXAMPLE 8

Production of the Strontium (II) Complex of L-ascorbic acid

A suspension of strontium carbonate (1.0 g, 6.77 mmol) and L-ascorbic acid (2.39 g, 13.5 mmol) in water (25 ml) was stirred at 80° C. for seven hours. The mixture became yellow. The mixture was filtered at room temperature, and the filtrate was evaporated to dryness and dried in vacuo at ambient temperature. The title compound was isolated as a yellow powder. Yield 2.50 g (78%). Melting point approx. 250° C.

EXAMPLE 9

Production of the Strontium (II) Complex of L-ascorbic acid 6-palmitate

A solution of strontium chloride hexahydrate (0.32 g, 1.2 mmol) in water (3 ml) was added to a stirred solution of L-ascorbic acid 6-palmitate (1.0 g, 2.4 mmol) in ethanol/water (100 ml, 50:50 (volume)) at room temperature. The mixture was stirred for 5 minutes and the title compound was isolated by filtration and dried by freeze-drying. Yield 0.514 g (47%). White powder.

EXAMPLE 10

Production of Strontium Ibuprofen Salt

Ibuprofen (2.59 g, 12.5 mmol) was dissolved in water (100 ml) containing sodium hydroxide (0.503 g, 12.5 mmol). A solution of strontium chloride hexahydrate (1.68 g, 6.3 mmol) in water (5 ml) was added. The mixture was stirred for 10 minutes at room temperature and the title compound was isolated by filtration and dried. Yield 1.30 g (44%). Melting point >300° C.

EXAMPLE 11

Production of Strontium Diclofenac Salt

Diclofenac (0.35 g, 1.18 mmol) was dissolved in water/ethanol (30 ml, 50:50 (volume)) containing sodium hydroxide (24 mg, 0.59 mmol). A solution of strontium chloride hexahydrate (0.16 g, 0.59 mmol) in water (3 ml) was added.

The mixture was stirred for 20 minutes, and the title compound was isolated by filtration and dried. Yield 0.122 g (15%).

EXAMPLE 12

Preparation of Strontium Stearate

Stearic acid (2.97 g, 10.4 mmol) was dissolved in water/ethanol (100 ml, 50:50 (volume)) containing sodium hydroxide (0.417 g, 10.4 mmol). The mixture was heated to 70° C. and a solution of strontium chloride hexahydrate (1.39 g, 5.2 mmol) in water (3 ml) was added. The title compound was isolated by centrifugation of the formed precipitate. Yield 1.6 g (46%).

EXAMPLE 13

Production of SrEDTA Dimeglumine Salt

Strontium EDTA (1 g, 2.65 mmol) (from Example 4) and N-methyl-D-glucamine (1.03 g, 529 mmol) were dissolved in water (10 ml) and stirred at 70° C. for 30 minutes. The mixture was filtered and the filtrate was evaporated to dryness and dried in vacuo at ambient temperature. The title compound was isolated as white crystalline material. Yield 0.722 g (36%).

EXAMPLE 14

Production of Strontium Benzoate

Strontium carbonate (1.0 g, 6.77 mmol) and benzoic acid (1.65 g, 13.5 mmol) in water (30 ml) were stirred for 4 hours at 70° C. The mixture was filtered and the fitrate was evaporated to dryness and dried in vaccuo at ambient temperature. The title compound was isolated. Yield 1.8 g (81%).

EXAMPLE 15

Production of Strontium Glutarate

Strontium carbonate (1.0 g, 6.77 mmol) and glutaric acid (0.89 g, 6.77 mmol) in water (30 ml) were stirred over night at 70° C. The mixture was filtered and the filtrate was evaporated to dryness and dried in vaccuo at ambient temperature. The title compound was isolated. Yield 1.23 g (83%).

EXAMPLE 16

Production of Strontium Alanine Salt

Strontium hydroxide octahydrate (1.0 g, 3.79 mmol) and L-alanine (0.67 g, 7.52 mmol) in water (30 ml) were stirred for 4 hours at room temperature. The mixture was filtered and the filtrate was evaporated to dryness and dried in vaccuo at ambient temperature. Yield 0.81 g (63%).

EXAMPLE 17

Production of Strontium Hippurate

Strontium carbonate (0.5 g, 3.39 mmol) and hippuric acid (1.215 g, 6.77 mmol) in water (30 ml) were stirred at 70° C. for 5 hours. The mixture was filtered and the filtrate was evaporated to dryness and dried in vacuo at ambient temperature. Yield 1.25 g (83%).

EXAMPLE 18

Production of a Strontium Chelate with 1,2-di(2-amino-ethoxy) ethane-N,N,N',N'-tetraacetic acid Strontium carbonate (1.0 g, 6.77 mmol) and 1,2-di(2-amino-ethoxy)ethane-N,N,N',N'-tetraacetic acid (2.58 g, 6.77 mmol) in water (30 ml) were stirred at 85° C. for 48 hours. The mixture was evaporated and the title compound dried in vaccuo at ambient temperature. Yield 2.55 g (81%).

The compounds of Examples 4 to 18 may be formulated for administration in any convenient form (e.g. gels, creams, solutions, tablets, etc) using conventional pharmaceutical carriers and excipients.

EXAMPLE 19

Skin Penetration Composition

A strontium-containing composition was prepared by dissolving 40 g strontium chloride hexahydrate in 1000 ml solvent. The composition of the solvent was:

50% (volume) distilled water
25% (volume) Tetraglycol® (glucofurol)
25% (volume) DMSO Two patients with Bechterev disease had been using non-steroidal anti-inflammatory drugs and opioids without pain relief in the iliosacral joints. The composition of this Example was administered dermally at the iliosacral joints, two-three times daily. Both patients observed a complete relief of pain.

EXAMPLE 20

Solution for Injection

Strontium EDTA dimeglumine salt (20 mg) from Example 13 was dissolved in a 0.9% sterile aqueous solution (10 ml) and filled in a 10 ml vial (injection vial with rubber stopper). The solution was sterilised by autoclaving. The solution contained 0.2 mg strontium per ml.

EXAMPLE 21

Hydrogel Containing Ibuprofen, Strontium Ascorbate and Skin Penetration Enhancer Strontium ascorbate (900 mg) from Example 8 and sodium lauryl sulphate (450 mg) were mixed into Ibux gel 5% (produced by Weifa AS, Oslo, Norway) using a mortar and pestle. (Ibux gel contains 5% ibuprofen in a hydrogel comprising hydroxyethylcellulose, benzylalcohol, isopropanol, sodium hydroxyl and purified water). The resulting gel contained 1.2% wt strontium.

EXAMPLE 22

Hydrogel Comprising Ibuprofen and Strontium Chloride

Strontium chloride hexahydrate (0.8 g) was mixed into Ibux gel 5% (19.2 g) using a mortar and pestle.

EXAMPLE 23

Mucoadhesive Hydrogel Comprising Ibuprofen and Strontium Chloride

Polyacrylic acid 5100 sodium salt (Fluka 81132) (0.21 g) was mixed into a hydrogel comprising ibuprofen and strontium (see Example 22) (7.0 g) using a mortar and pestle.

EXAMPLE 24

Mucoadhesive Hydrogel Comprising Ibuprofen and Strontium Chloride

Strontium chloride hexahydrate (1.5 g) and chitosan malate (203-490-14SM from FMC Biopolymers, Drammen, Norway) (0.75 g) were mixed into Ibux gel 5% (12.75 g). The resulting mucoadhesive gel contained 3.3% wt strontium and 5% wt ibuprofen.

EXAMPLE 25

Cream Containing Strontium Chloride

Strontium chloride hexahydrate (1.2 g) was mixed into Unguentum Merck (13.8 g) using a mortar and pestle. The cream contained 2.6% wt strontium in the form of strontium chloride.

EXAMPLE 26

Cream Containing Strontium Chloride and a Skin Penetration Enhancer

Strontium chloride hexahydrate (1.2 g) and sodium lauryl sulphate. (0.3 g) were mixed into Unguentum Merck (13.5 g) using a mortar and pestle. The cream contained 2.6% wt strontium in the form of strontium chloride.

EXAMPLE 27

Cream Containing Lidocaine and Strontium Diclofenac Salt

Strontium diclofenac (40 mg) from Example 11 was mixed into Xylocain® 5% cream (Astra Zeneca AS, Oslo, Norway) using a mortar and pestle. (100 g Xylocain® 5% cream contains 5 g lidocaine in coconut oil 13.8 g, polyoxyethylene ester 4.5 g, carboxypolymethylene 1 g, sodium hydroxide 6.5 g and purified water 69 g). The cream contained 5% wt lidocaine and 40 mg/g strontium diclofenac.

EXAMPLE 28

Ointment Containing Hydrocortisone and Strontium Stearate

Strontium stearate (60 mg) from Example 12 was mixed into Hydrokortison 1% ointment (Galderma Nordic AB) using a mortar and pestle (Hydrokortison 1% ointment contains 1% hydrocortisone, propyleneglycol, liquid paraffin, cetylalcohol and Vaseline®). The resulting ointment contained 1% wt hydrocortisone and 3% wt strontium stearate.

EXAMPLE 29

Mucoadhesive Formulation Containing Strontium Ibuprofen

Strontium ibuprofen (0.5 g) from Example 10 was mixed into Orabase® paste (Squibb AB, Lidingö, Sweden) (14.5 g) using a mortar and pestle. Orabase® contains gelatin, pectin, sodium carboxymethhylcellulose, polyethylene and liquid paraffin. The resulting formulation contained 3.3% wt strontium ibuprofen and is useful for treatment of pain in the mouth or other mucosal body surfaces.

EXAMPLE 30

Clinical Testing of the Composition of Example 19

A 35 year old woman was involved in a car accident seven years earlier and had developed severe pain in the neck and shoulders. The patient had used non-steroidal anti-inflammatory drugs for a long time without significant effect. She had not slept continuously any night since the accident.

The patient tried the composition of Example 19 by administering topically to the areas of pain. She claimed a pain relieving effect after one minute and had no or very little pain for the following 2 to 3 days. After administration of the composition of Example 13 she was able to sleep for about 10 hours each of the next two nights.

EXAMPLE 31

Clinical Testing of the Composition of Example 19

Nine boxers with pain in the face and/or fingers have tested out the effect of the composition of Example 19. The composition was administered directly onto the painful area. An immediate relief of pain was observed for all painful areas by these boxers. The pain reduction was present for a long time.

Four boxers with pain in the nose and eye area tested the effects of a composition which was a 2% wt formulation of strontium chloride hexahydrate in the same solvent as in Example 19 (i.e. 50% of the strontium concentration in Example 19). This formulation also showed good clinical effects both with regard to pain relief and reduction of swelling of the painful area.

EXAMPLE 32

Clinical Testing of Composition from Example 19

A patient with pain in the pelvic area as a result of lack of ligaments during pregnancy had tried non-steroidal anti-inflammatory drug treatment for some time without any effect.

The topical formulation of Example 19 was applied and resulted in an immediate reduction in pain. The pain relief effect extended for about six hours per application.

EXAMPLE 33

Clinical Testing of Composition from Example 19

Two patients with herpes simplex infection in the mouth area had previously used antiviral cream (Zovirax® (acylovir)) with moderate effect. The effect of the antiviral treatment was an improvement in the progress of the disease, but lesions were present for seven to ten days (as without treatment).

These two patients have now used the composition of Example 19 during eight different outbreaks of lesions. Local administration of the composition totally stopped the development of the lesions and dried out lesions which had formed.

The invention claimed is:

1. A method of treatment of a human or mammalian subject experiencing chronic pain in sub-dermal soft tissue to combat said chronic pain, said method comprising administering topically to said subject an effective amount of a pain-relieving topical pharmaceutical composition comprising:

(a) a physiologically tolerable strontium compound, (b) a physiologically tolerable carrier, (c) dimethylsulphoxide, and (d) glycofurol.

2. The method as claimed in claim 1, wherein said strontium compound is selected from the group consisting of strontium chloride, strontium nitrate, strontium acetate, strontium citrate, strontium lactate and strontium hydrogen-phosphate.

3. The method as claimed in claim 1, wherein said strontium compound is strontium chloride.

4. The method as claimed in claim 1, wherein said carrier is water.

5. The method as claimed in claim 1, wherein said composition comprises strontium chloride, water, dimethyl-sulphoxide and glycofurol.

6. A topical pain relieving pharmaceutical composition comprising:

(a) a physiologically tolerable strontium compound, (b) a physiologically tolerable carrier, (c) dimethylsuiphoxide, and (d) glycofurol.

7. The composition as claimed in claim 6, wherein said composition comprises strontium chloride, water, dimethyl-sulphoxide and glycofurol.

* * * * *